United States Patent [19]

Ichiki et al.

[11] 4,280,835
[45] Jul. 28, 1981

[54] HERBICIDAL N-PHENYL-N-METHYLUREA DERIVATIVES

[75] Inventors: Takemoto Ichiki, Takarazuka; Ryo Yoshida, Kawanishi; Seizo Sumida, Nishinomiya; Kamoshita Katsuzo, Osaka, all of Japan

[73] Assignee: Sumitomo Chemical Company, Limited, Osaka, Japan

[21] Appl. No.: 967,018

[22] Filed: Dec. 6, 1978

[30] Foreign Application Priority Data

Dec. 13, 1977 [JP] Japan ................... 52-150377
Dec. 17, 1978 [JP] Japan ................... 53-128096

[51] Int. Cl.³ .................................. A01N 47/30
[52] U.S. Cl. ......................... 71/120; 424/322; 260/453 RW; 564/52
[58] Field of Search ............ 71/120; 260/453 RW, 260/553 A

[56] References Cited

U.S. PATENT DOCUMENTS

| | | | |
|---|---|---|---|
| 2,723,193 | 11/1955 | Todd | 71/120 |
| 3,119,682 | 1/1964 | Martin et al. | 71/120 |
| 3,769,341 | 10/1973 | Alt | 71/120 |
| 3,865,571 | 2/1975 | Schuler | 71/120 |
| 4,129,436 | 12/1978 | Takemoto et al. | 71/120 |
| 4,144,049 | 3/1979 | Yoshida et al. | 71/120 |

FOREIGN PATENT DOCUMENTS 42-6833  3/1967 Japan.

*Primary Examiner*—Catherine L. Mills
*Attorney, Agent, or Firm*—Birch, Stewart, Kolasch & Birch

[57] ABSTRACT

Novel N'-4-(2-naphthyloxy)phenyl-N-methylurea derivatives of the formula:

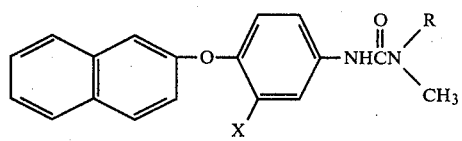

wherein X is a hydrogen atom, a halogen atom or a trifluoromethyl group and R is a methyl or methoxy group having a herbicidal activity, particularly effective in exterminating weeds in the cultivation of soybean and gramineous crops such as wheat and barley, and/or having a fungicidal activity especially effective in controlling the rust of wheat and barley.

9 Claims, No Drawings

HERBICIDAL N-PHENYL-N-METHYLUREA DERIVATIVES

The present invention relates to N'-4-(2-naphthyloxy)phenyl-N-methylurea derivatives of the formula:

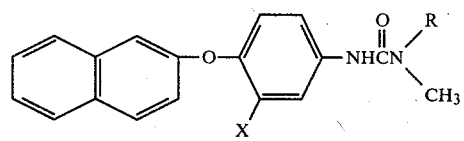

wherein X is a hydrogen atom, a halogen atom or a trifluoromethyl group and R is a methyl group or a methoxy group, and their production and use.

Soybeans, peanuts, cotton, corn, wheat, rice, sugar beets and the like are crops of world-wide importance and, in the cultivation of these crops, chemical control of weeds is necessary to prevent reductions in the yield.

Among substituted urea derivatives, as is well known, there are compounds having a strong herbicidal activity, such as N'-4-chlorophenyl-N,N-dimethylurea (monuron) and N'-3,4-dichlorophenyl-N,N-dimethylurea (diuron). It is also well known that the herbicidal activity of these urea derivatives is due to the inhibition of photosynthesis. Photosynthesis is a physiological function peculiar to higher plants and does not take place in mammals. Accordingly, specific inhibitors of the photosynthetic process usually cause no significant harm to mammals but can be extremely effective in the extermination of higher plants. In fact, herbicidal photosynthesis inhibitors such as monuron, diuron, 5-bromo-3-sec-butyluracil (bromacil) and the like are all low in mammalian toxicity. However, they exert a herbicidal activity against all higher plants, i.e. crops and weeds alike, since photosynthesis is common to all of the higher plants. Thus, most photosynthesis inhibitors are nonselective and damage crop plants.

For a compound to be a selective herbicide, it has to have both a strong herbicidal activity against weeds and a high level of selectivity to the intended crop. However, such selective herbicides are very difficult to find and can not easily be predicted by mere analogy and modification of known chemical structures. Therefore, a highly detailed study with trial and error is necessary to find such selective herbicides. Selective herbicidal activity requires a very specific chemical structure, and only a slight difference in the chemical structure produces quite a large difference in the degree and kind of selectivity.

It has now been found that the compounds of the formula (I) show a remarkable herbicidal activity with no phytotoxicity to rice plants in paddy fields by soil treatment after transplantation. Besides, they can safely be used in upland fields without phytotoxicity to rice plants, wheat, corn, soybeans, peanuts, cotton and sugar beets by preemergence application. The greatest characteristic of the present invention is that excellent foliar-applied herbicides which can safely be applied to wheat and soybean can be provided. That is, when the compounds (I) are applied to a wheat field as a foliar-applied agent, they can exterminate with little phytotoxicity to wheat a wide range of weeds such as water foxtail (*Alopecurus aequalis*), large crabgrass (*Digitaria sanguinalis*), black nightshade (*Solanum nigrum*), common lambsquarters (*Chenopodium album*), shepard's-purse (*Capsella bursa pastoris*), catchweed bedstraw (*Galium aparine* L.) and chickweed (*Stellaria media*), including wild oat (*Avena fatua* L.) which is regarded as most difficult to exterminate. When the compounds (I) are applied to soybean fields, they can exterminate many weeds such as large crabgrass (*Digitaria sanguinalis*), cocklebur (*Xanthium pennsylvanicum*), annual morning-glory (*Ipomoea purpurea*), jimsonweed (*Datura stranomium*), sunflower (*Helianthus annuus*) and redroot pigweed (*Amaranthus retroflexus*), with little phytotoxicity to soybean.

These excellent properties of the compounds (I) result from the following characteristics in chemical structure: they have (1) a 2-naphthyloxy group as a substituent and (2) an N-methoxy-N-methyl group or an N,N-dimethyl group. For example, in comparison with N'-4-phenoxy-3-chlorophenyl-N,N-dimethylurea [control (a); described in Swiss Pat. No. 507,646], N'-4-(1-naphthyloxy)-phenyl-N,N-dimethylurea [control (b)] and N'-4-(2-naphthyloxy)-phenyl-N-methylurea [control (c)], it is apparent that the compounds (I) are far superior in herbicidal activity and selectivity, as is partly shown in the examples hereinafter set forth.

As described above, the compounds (I) are very useful as selective herbicides for crop lands and besides they can be used as excellent herbicides for non-crop lands on account of their strong herbicidal activity.

In addition, it may be noted that the compounds (I) are effective in prevention and inhibition of plant diseases caused by various phytopathogenic fungi in crop plants and fruit trees such as powdery mildew in apples, grapes, oranges, cucumbers, melons, wheat, etc., downy mildew in grapes, oranges, cucumbers, melons, etc., yellows in root crops and rust in wheats, beans, etc. They are particularly effective in prevention and inhibition of rust such as stripe rust in barleys and wheats caused by *Puccinia striiformis*, stem rust in barleys and wheats caused by *Puccinia graminis*, leaf rust in wheats caused by *Puccinia recondita*, crown rust in oats caused by *Puccinia coronata*, rust in soybeans caused by *Uromyces sojae*, rust in kidney beans caused by *Uromyces appendiculatus* and rust in coffee caused by *Hemileia vastatrix*. Compared with conventional fungicides, the compounds (I) are characteristic in having not only a prevention effect but also a curative effect.

Accordingly, the compounds (I) of the present invention are useful as herbicides and/or fungicides. Particularly when they are used in cultivation of paddy rice plants, upland rice plants, cotton, soybeans, corn, wheat, barley, etc., the simultaneous production of a herbicidal action and a fungicidal action can be expected.

The compounds (I) are novel and can be produced, for instance, by the following procedures:

Procedure A

The compound (I) is obtainable by reacting a 4-(2-naphthyloxy)phenylisocyanate of the formula:

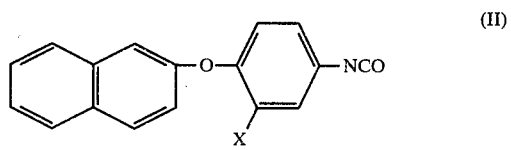

wherein X is a hydrogen atom, a halogen atom or a trifluoromethyl group with N,O-dimethylhydroxylamine or dimethylamine.

The reaction may be carried out in an organic solvent (e.g. benzene, toluene, xylene, diethyl ether, tetrahydrofuran, dioxane, N,N-dimethylformamide, chloroform, carbon tetrachloride), water or mixtures thereof. The reaction is effected usually at a temperature of 0° to 50° C. and comes to an end in 1 to 10 hours.

Procedure B

The compound (I) is obtainable by reacting an N'-4-(2-naphthyloxy)phenyl-N-hydroxyurea of the formula:

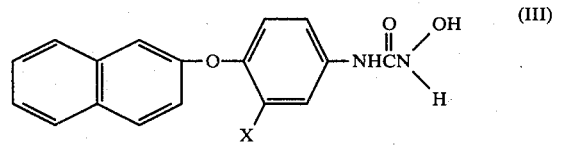

wherein X is a hydrogen atom, a halogen atom or a trifluoromethyl group with a methylating agent.

As the methylating agent, there may be used methyl iodide, dimethyl sulfate, diazomethane or the like. When dimethyl sulfate is used, for example, the reaction may be carried out in a solvent in the presence of an alkali. Examples of the alkali include sodium hydroxide and potassium hydroxide, and examples of the solvent are organic solvents (e.g. benzene, toluene, xylene, methanol, ethanol, isopropanol, diethyl ether, tetrahydrofuran, dioxane, methylene chloride), water and mixtures thereof. The existence of a phase transfer catalyst such as benzyltriethylammonium chloride or tetra-n-butylammonium bromide is advantageous for the reaction. The reaction is effected usually at a temperature of 0° to 100° C. and comes to an end in 1 to 10 hours.

Procedure C

The compound (I) is obtainable by reacting a 4-(2-naphthyloxy)aniline of the formula:

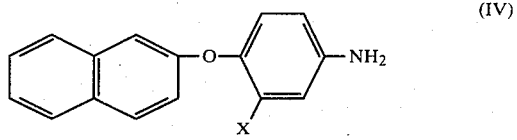

wherein X is a hydrogen atom, a halogen atom or a trifluoromethyl group with N-methoxy-N-methylcarbamyl chloride or dimethylcarbamyl chloride.

The reaction may be carried out in an organic solvent (e.g. benzene, toluene, xylene, diethyl ether, tetrahydrofuran, dioxane, chloroform, carbon tetrachloride, methylene chloride, ethyl acetate, N,N-dimethylformamide, mixtures thereof) in the presence of a dehydrohalogenating agent (e.g. pyridine, triethylamine, sodium hydroxide, potassium hydroxide, sodium carbonate). The reaction is effected usually at a temperature of 20° to 150° C. and comes to an end in 1 to 10 hours.

The starting compounds (II), (III) and (IV) in the above procedures may be prepared through the following steps:

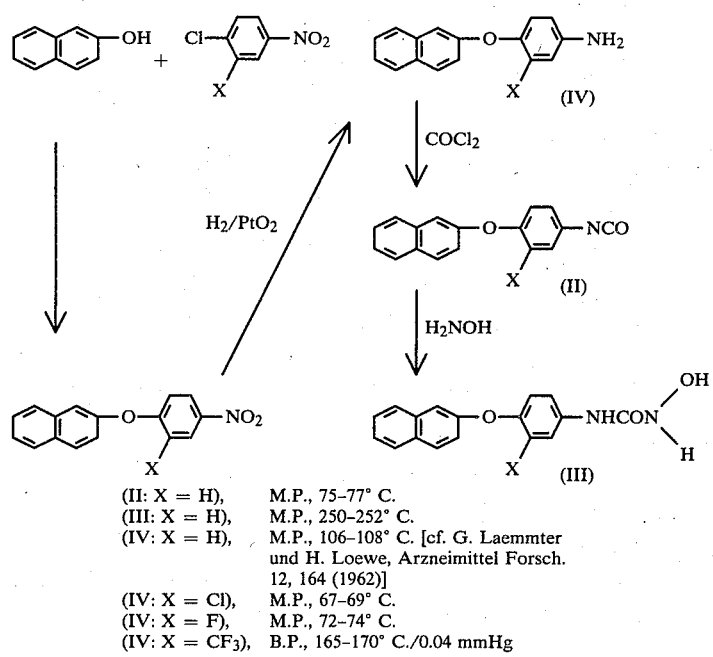

(II: X = H),    M.P., 75–77° C.
(III: X = H),   M.P., 250–252° C.
(IV: X = H),    M.P., 106–108° C. [cf. G. Laemmter und H. Loewe, Arzneimittel Forsch. 12, 164 (1962)]
(IV: X = Cl),   M.P., 67–69° C.
(IV: X = F),    M.P., 72–74° C.
(IV: X = CF$_3$), B.P., 165–170° C./0.04 mmHg wherein X is as defined above.

Namely, these conversions may be accomplished, for instance, by the following procedures:

Procedure D

The compound (IV) is obtainable by hydrogenating the corresponding nitro compound of the formula:

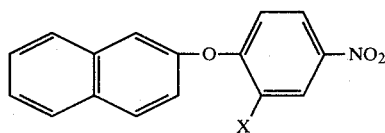

wherein X is as defined above.

The hydrogenation may be carried out by treatment of the compound (V) in an organic solvent (e.g. benzene, toluene, xylene, ethyl acetate, ethanol, mixtures thereof) with hydrogen in the presence of a catalyst (e.g. platinum oxide). The reaction is effected usually at a temperature of 20° to 50° C. and comes to an end in 1 to 10 hours.

Procedure E

The compound (II) is obtainable by reacting the compound (IV) with phosgene.

The reaction may be carried out in an organic solvent (e.g. benzene, toluene, xylene, diethyl ether, tetrahydrofuran, dioxane, chloroform, carbon tetrachloride, methylene chloride, ethyl acetate, N,N-dimethylformamide, mixtures thereof). It is effected usually at a temperature of 20° to 150° C. and comes to an end in 1 to 10 hours.

Procedure F

The compound (III) is obtainable by reacting the compound (II) with hydroxylamine.

The reaction may be carried out in an organic solvent (e.g. benzene, toluene, xylene, diethyl ether, tetrahydrofuran, dioxane, N,N-dimethylformamide, chloroform, carbon tetrachloride), water or mixtures thereof. It is effected usually at a temperature of 0° to 50° C. and comes to an end in 1 to 10 hours.

Some specific examples of the compound (I) will be shown below without any intention of limiting the scope of the invention thereto:

| Compound No. | Chemical structure | Physical property |
| --- | --- | --- |
| 1 | [naphthyl-O-phenyl-NHC(O)N(OCH3)(CH3)] | M.P., 102–103° C. |
| 2 | [naphthyl-O-phenyl-NHC(O)N(CH3)(CH3)] | M.P., 156–157° C. |
| 3 | [naphthyl-O-(Cl-phenyl)-NHC(O)N(OCH3)(CH3)] | $n_D^{25.0}$ 1.5860 |
| 4 | [naphthyl-O-(Cl-phenyl)-NHC(O)N(CH3)(CH3)] | M.P., 130–132° C. |
| 5 | [naphthyl-O-(F3C-phenyl)-NHC(O)N(OCH3)(CH3)] | M.P., 129–130° C. |
| 6 | [naphthyl-O-(F3C-phenyl)-NHC(O)N(CH3)(CH3)] | M.P., 210–211° C. |
| 7 | [naphthyl-O-(F-phenyl)-NHC(O)N(OCH3)(CH3)] | M.P., 100–101° C. |
| 8 | [naphthyl-O-(F-phenyl)-NHC(O)N(CH3)(CH3)] | M.P., 154–155° C. |

Practical and presently preferred embodiments of the preparation of the compounds (I) are illustratively shown in the following examples.

EXAMPLE 1 (Procedure A)

Thirteen grams of 4-(2-naphthyloxy)phenyl isocyanate were dissolved in 100 ml of benzene, and a solution of 4 g of N,O-dimethylhydroxylamine in 50 ml of benzene was added dropwise thereto at a temperature below 30° C. The reaction mixture was allowed to stand at room temperature for 30 minutes, and the solvent was then removed under reduced pressure. The residue was recrystallized from ethanol to obtain 14 g of N'-[4-(2-naphthyloxy)phenyl]-N-methoxy-N-methylurea as white needles. M.P., 102°–103° C.

Elementary analysis: Calcd. for $C_{19}H_{18}N_2O_3$: C, 70.79%; H, 5.63%; N, 8.69%. Found: C, 70.82%; H, 5.70%; N, 8.72%.

NMR$\delta_{CDCl_3}$: 3.10 (s, 3H), 3.66 (s, 3H), 6.80–7.90 (12H).

The starting compound in the above Example, i.e. 4-(2-naphthyloxy)phenyl isocyanate (B.P., 137° to 149° C./0.8 mmHg; M.P., 75° to 77° C.), was prepared by reducing 4-(2-naphthyloxy)nitrobenzene with hydrogen in the presence of platinum dioxide in an inert solvent and reacting the resultant 4-(2-naphthyloxy)aniline (M.P., 106° to 108° C.) with phosgene in an inert solvent.

EXAMPLE 2 (Procedure B)

Fourteen grams of 3-chloro-4-(2-naphthyloxy)phenyl isocyanate were dissolved in 60 ml of methylene chloride, and the resulting solution was added dropwise to 10 ml of an aqueous solution containing 4 g of hydroxylamine at a temperature below 20° C. Precipitated crystals were collected on a filter, washed with water and dried to obtain 13.5 g of N'-[3-chloro-4-(2-naphthyloxy)phenyl]-N-hydroxyurea. Thereafter, 13.5 g of the product was dissolved in 150 ml of a benzene-methanol (1:1) mixture, and 13 ml of dimethyl sulfate and 30 ml of 10 N sodium hydroxide were alternately added dropwise thereto at a temperature below 30° C. After stirring at room temperature, the reaction mixture was diluted with water, followed by extraction with benzene. The benzene layer was washed with water, and the solvent was removed under reduced pressure. The oily substance obtained was purified by column chromatography (silica gel, 100–120 mesh; eluting solvent, tetrahydrofuran-benzene (1:1) mixture) to obtain 7.3 g of N'-[3-chloro-4-(2-naphthyloxy)phenyl]-N-methoxy-N-methylurea. $n_D^{25.0}$:1.5860.

Elementary analysis: Calcd. for $C_{19}H_{17}ClN_2O_3$: C, 63.95%; H, 4.80%; N, 7.85%; Cl, 9.94%. Found: C, 63.72%; H, 4.68%; N, 7.88%; Cl, 10.01%.

NMR$\delta_{CDCl_3}$: 3.15 (s, 3H), 3.71 (s, 3H), 6.80–7.90 (11H).

The starting compound in the above Example, i.e. 3-chloro-4-(2-naphthyloxy)phenyl isocyanate, was prepared by reducing 3-chloro-4-(2-naphthyloxy)nitrobenzene with hydrogen in the presence of platinum dioxide in an inert solvent and reacting the resultant 3-chloro-4-(2-naphthyloxy)aniline (B.P., 173° to 198° C./0.2 mmHg; M.P., 67° to 69° C.) with phosgene in an inert solvent.

EXAMPLE 3 (Procedure C)

Twenty-five grams of 4-(2-naphthyloxy)aniline were dissolved in 200 ml of toluene, and 100 ml of 40% aqueous sodium hydroxide solution and 12 g of N,N-dimethylcarbamyl chloride were added thereto. The reaction mixture was heated under reflux for 10 hours, and its temperature was cooled to room temperature. The toluene layer was washed with water, and the solvent was removed under reduced pressure. The residue was recrystallized from ethanol to obtain 18 g of N'-[4-(2-naphthyloxy)phenyl]-N,N-dimethylurea as white needles. M.P., 156°–157° C.

Elementary analysis: Calcd. for $C_{19}H_{18}N_2O_2$: C, 74.49%; H, 5.92%; N, 9.15%. Found: C, 74.60%; H, 5.92%; N, 8.96%.

NMR$\delta_{CDCl_3}$: 2.95 (s, 6H), 4.36 (s, 1H), 6.80-7.80 (11H).

EXAMPLE 4 (Procedure A)

Five grams of 3-trifluoromethyl-4-(2-naphthyloxy)phenyl isocyanate were dissolved in 100 ml of benzene, and a solution of 2 g of N,O-dimethylhydroxylamine in 50 ml of benzene was added dropwise thereto at a temperature below 30° C. The reaction mixture was allowed to stand at room temperature for 30 minutes, and the solvent was then removed under reduced pressure. The residue was recrystallized from ethanol to obtain 4.2 g of N'-[3-trifluoromethyl-4-(2-naphthyloxy)phenyl]-N-methoxy-N-methylurea as white needles. M.P. 129°–130° C.

Elementary analysis: Calcd. for $C_{20}H_{17}O_3N_2F_3$: C, 61.53%; H, 4.39%, N, 7.18%. Found: C, 61.46%; H, 4.39%; N, 7.18%.

NMR$_{CDCl_3}$: 3.16 (s, 3H), 3.71 (s, 3H), 6.80-7.90 (11H).

The starting compound in the above Example, i.e. 3-trifluoromethyl-4-(2-naphthyloxy)phenyl isocyanate, was prepared by reducing 3-trifluoromethyl-4-(2-naphthyloxy)-nitrobenzene with hydrogen in the presence of platinum dioxide in an inert solvent and reacting the resultant 3-trifluoromethyl-4-(2-naphthyloxy)aniline (B.P., 143° to 176° C./0.04 mmHg) with phosgene in an inert solvent.

EXAMPLE 5 (Procedure B)

3-Trifluoromethyl-4-(2-naphthyloxy)phenyl isocyanate (16.5 g) was dissolved in 100 ml of methylene chloride, and the resulting solution was added dropwise to 10 ml of an aqueous solution containing 4 g of hydroxylamine at a temperature below 20° C. Precipitated crystals were collected on a filter, washed with water and dried to obtain 17.7 g of N'-[3-trifluoromethyl-4-(2-naphthyloxy)phenyl]-N-hydroxyurea. Thereafter, 17.7 g of the product and 12.5 g of dimethyl sulfate were dissolved in 200 ml of toluene, and after addition of 0.16 g of tetra-n-butylammonium bromide to the mixture, 11 ml of 10 N sodium hydroxide were dropwise added thereto at 20°–22° C. After stirring at room temperature, the reaction mixture was diluted with water, followed by extraction with benzene. The benzene layer was washed with water, and the solvent was removed under reduced pressure. The oily substance obtained was purified by column chromatography (silica gel, 100–200 mesh; eluting solvent, tetrahydrofuran-benzene (1:3) mixture) to obtain 16.2 g of N'-[3-trifluoromethyl-4-(2-naphthyloxy)phenyl]-N-methoxy-N-methylurea.

The product was confirmed to be the same product as obtained in Example 1 by IR, NMR, TLC and melting point.

EXAMPLE 6 (Procedure C)

3-Trifluoromethyl-4-(2-naphthyloxy)aniline (9.1 g) was dissolved in 200 ml of toluene, and 30 ml of 40% aqueous sodium hydroxide solution and 6.5 g of N,N-dimethylcarbamyl chloride were added thereto. The reaction mixture was heated under reflux for 10 hours and then cooled to room temperature. The toluene layer was washed with water, the solvent was removed by distillation under reduced pressure and the residue was recrystallized from ethanol to obtain 5.1 g of N'-[3-trifluoromethyl-4-(2-naphthyloxy)phenyl]-N,N-dimethylurea as white needles. M.P. 210°–211° C.

Elementary analysis: Calcd. for $C_{20}H_{17}O_2N_2F_3$: C, 64.16%; H, 4.58%; N, 7.48%. Found: C, 64.23%; H, 4.59%; N, 7.46%.

NMR$\delta_{CDCl_3\text{-}DMSO\text{-}d_6}$: 3.10 (s, 6H), 6.70-8.00 (10H), 8.55 (s, 1H).

EXAMPLE 7 (Procedure D)

3-Chloro-4-(2-naphthyloxy)nitrobenzene (14.8 g) and platinum dioxide (0.1 g) were suspended in a mixture of benzene and ethanol (1:1) (200 ml), and hydrogenation was carried out until 3.2 liters of hydrogen were absorbed. After removal of the solvent from the reaction mixture by distillation under reduced pressure, the residue was distilled in vacuo to give 3-chloro-4-(2-naphthyloxy)aniline (8 g) as a fraction boiling at 173° to 198° C./0.2 to 0.3 mmHg. M.P., 67°–69° C.

EXAMPLE 8 (Procedure E)

A solution of 4-(2-naphthyloxy)aniline (4 g) in toluene (100 ml) was dropwise added to a solution of phosgene (3.5 g) in toluene (50 ml), and the resulting mixture was refluxed for 1 hour. After removal of the solvent from the reaction mixture by distillation under reduced pressure, the residue was distilled in vacuo to give 4-(2-naphthyloxy)phenyl isocyanate (4.1 g) as a fraction boiling at 137° to 149° C./0.8 mmHg. M.P., 75°–77° C.

EXAMPLE 9 (Procedure F)

To a solution of hydroxylamine sulfate (8.21 g) in water (50 ml) and toluene (100 ml), 10 N sodium hydroxide solution (9.5 ml) was dropwise added at 10° C. A solution of 4-(2-naphthyloxy)phenyl isocyanate (13 g) in toluene (50 ml) was dropwise added thereto at 10° to 12° C. for 2 hours, during which stirring was continued. After the dropwise addition, the reaction mixture was stirred at 25° C. for 2 hours. The precipitated crystals were collected by filtration, washed with water and washed with toluene to give N'-4-(2-naphthyloxy)-phenyl-N-hydroxyurea (14 g). M.P., 106°–108° C.

In the practical usage of the compounds (I), they may be applied as such or in any preparation form such as wettable powders, emulsifiable concentrates, granules, fine granules or dusts.

In producing such preparation form, a solid or liquid carrier may be used. As for the solid carrier, there may be mentioned mineral powders (e.g. kaolin, bentonite, clay, montmorillonite, talc, diatomaceous earth, mica, vermiculite, gypsum, calcium carbonate, apatite), vebetable powders (e.g. soybean powder, flour, wooden powder, tobacco powder, starch, crystalline cellulose) high molecular weight compounds (e.g. petroleum resin, polyvinyl chloride, dammar gum, ketone resin), alumina, wax and the like.

As for the liquid carrier, there may be mentioned alcohols (e.g. methyl alcohol, ethyl alcohol, ethylene glycol, benzyl alcohol), aromatic hydrocarbons (e.g. toluene, benzene, xylene, methylnaphthalene), halogenated hydrocarbons (e.g. chloroform, carbon tetrachloride, monochlorobenzene), ethers (e.g. dioxane, tetrahydrofuran), ketones (e.g. acetone, methyl ethyl ketone, cyclohexanone), esters (e.g. ethyl acetate, butyl acetate, ethylene glycol acetate), acid amides (e.g. dimethylformamide), nitriles (e.g. acetonitrile), ether alcohols (e.g. ethylene glycol ethyl ether), water and the like.

A surface active agent used for emulsification, dispersion or spreading may be any of the non-ionic, anionic, cationic and amphoteric type of agents. Examples of the surface active agent include polyoxyethylene alkyl ethers, polyoxyethylene alkylaryl ethers, polyoxyethylene fatty acid esters, sorbitan fatty acid esters, polyoxyethylene sorbitan fatty acid esters, oxyethylene polymers, oxypropylene polymers, polyoxyethylene alkyl phosphates, fatty acid salts, alkyl sulfates, alkyl sulfonates, alkylaryl sulfonates, alkyl phosphates, quaternary ammonium salts and the like. But, the surface active agent is not of course limited to these compounds. And, if necessary, gelatin, casein, sodium alginate, starch, agar, polyvinyl alcohol or the like may be used as an auxiliary agent.

In the preparation of a herbicidal composition, the content of the compound (I) may be from 1 to 95% by weight, preferably from 5 to 80% by weight.

Practical embodiments of the herbicidal composition according to the invention are illustratively shown in the following examples wherein parts and % are by weight.

Preparation Example 1

Eighty parts of Compound No. 1 or 5, 5 parts of polyoxyethylene alkylaryl ether and 15 parts of synthetic silicon oxide hydrate are well mixed while being powdered to obtain a wettable powder.

Preparation Example 2

Thirty parts of Compound No. 2 or 6, 7 parts of polyoxyethylene alkylaryl ether, 3 parts of alkylaryl sulfonate and 60 parts of xylene are well mixed to obtain an emulsifiable concentrate.

Preparation Example 3

One part of Compound No. 3 or 6, 1 part of white carbon, 5 parts of ligninsulfonate and 93 parts of clay are well mixed while being powdered. The mixture is then well kneaded with water, granulated and dried to obtain a granule.

Preparation Example 4

Fourty parts of bentonite, 5 parts of ligninsulfonate and 55 parts of clay are well mixed while being powdered. The mixture is then well kneaded with water, granulated and dried to obtain a granule containing no active ingredient. The granule is then impregnated with 5 parts of Compound No. 4 or 5 to obtain a granule.

Preparation Example 5

Three parts of Compound No. 1 or 5, 0.5 part of isopropyl phosphate, 66.5 parts of clay and 30 parts of talc are well mixed while being powdered to obtain a dust.

The compounds (I) of the invention may be used together with other herbicides to improve their activity as herbicides, and in some cases, a synergistic effect can be expected. As the other herbicides, there may be exemplified phenoxy series herbicides such as 2,4-dichlorophenoxyacetic acid and 2,4-dichlorophenoxybutyric acid (including esters and salts thereof); diphenyl ether series herbicides such as 2,4-dichlorophenyl-4'-nitrophenyl ether, 2,4-dichlorophenyl-4'-nitro-3'-methoxyphenyl ether, 2,4-dichlorophenyl-3'-methoxycarbonyl-4'-nitrophenyl ether and 2-chloro-4-trifluoromethylphenyl-3'-hydroxycarbonyl-4'-nitrophenyl ether; triazine series herbicides such as 2-chloro-4,6-bisethylamino-1,3,5-triazine, 2-chloro-4-ethylamino-6-isopropylamino-1,3,5-triazine and 2-methylthio-4,6-bisethylamino-1,3,5-triazine; urea series herbicides such as 3-(3,4-dichlorophenyl)-1,1-dimethylurea, 3-(3,4-dichlorophenyl)-1-methoxy-1-methylurea, 3-[4-(4-chlorophenoxy)phenyl]-1,1-dimethylurea and 3-($\alpha,\alpha,\alpha$-trifluoro-m-tolyl)-1,1-dimethylurea; carbamate series herbicides such as isopropyl-N-(3-chlorophenyl)carbamate, methyl-N-(3,4-dichlorophenyl)carbamate and 4-chloro-2-butynyl-m-chlorocarbanilate; thiolcarbamate series herbicides such as S-(4-chlorobenzyl)-N,N-diethylthiolcarbamate and S-ethyl dipropylthiolcarbamate; acid anilide series herbicides such as 3,4-dichloropropionanilide, N-methoxymethyl-2,6-diethyl-2-chloroacetanilide and 2-chloro-2',6'-diethyl-N-(butoxymethyl)acetanilide; uracil series herbicides such as 5-bromo-3-sec-butyl-6-methyluracil and 3-cyclohexyl-5,6-trimethyleneuracil; pyridinium salt series herbicides such as 1,1'-dimethyl-4,4'-bispyridinium dichloride; phosphorus series herbicides such as N-(phosphonomethyl)glycine, O-methyl-O-(2-nitro-4-methylphenyl)-N-isopropylphosphoroamidothioate and O-ethyl-O-(2-nitro-5-methylphenyl)-N-sec-butylphosphoroamidothioate; toluidine series herbicides such as $\alpha,\alpha,\alpha$-trifluoro-2,6-dinitro-N,N-dipropyl-p-toluidine; N-sec-butyl-4-tert-butyl-2,6-dinitroaniline; 3,5-dinitro-$N^4,N^4$-dipropylsulfanylamide; 5-tert-butyl-3-(2,4-dichloro-5-isopropoxyphenyl)-1,3,4-oxadiazolin-2-one; 3-isopropyl-1H-2,1,3-benzothiadiazine(4)-3H-one-2,2-dioxide (including salts thereof); 2-($\beta$-naphthoxy)propionanilide; 2-($\alpha$-naphthoxy)-N,N-diethylpropionanilide; 3-amino-2,5-dichlorobenzoic acid; 2-sec-butyl-4,6-dinitrophenol; N-1-naphthylphthalamic acid; 2-[1-(N-allyloxyamino)butylidene-5,5-dimethyl-4-methoxycarbonylcyclohexane-1,3-dione (including salts thereof); 2-[4-(3,5-dichloropyridine-2-hydroxy)-phenoxy]propionic acid (including salts thereof); 2-[4-(2,4-dichlorophenoxy)phenoxy]propionic acid (including esters and salts thereof), ethyl N-benzoyl-N-(3,4-dichlorophenyl)-2-aminopropionate, methyl N-benzoyl-N-(3-chloro-4-fluorophenyl)-2-aminopropionate, ethyl N-benzoyl-N-(3-chloro-4-fluorophenyl)-2-aminopropionate, 1,2-dimethyl-3,5-diphenyl-1H-pyrazolium methyl sulfate and the like. But, the herbicides are not of course limited to these examples.

The herbicides of the invention may be applied together with fungicides, pyrethroid series insecticides, other insecticides, plant growth regulators, fertilizers, etc.

The dosage rate of the compounds (I) depends upon their kinds, the sorts of cultivated plants, the method of application, etc. Generally, however, the dosage rate is from 2 to 100 grams, preferably from 5 to 40 grams, of the active ingredient per are.

The application of the compounds (I) as herbicides will be illustrated in the following Examples wherein the phytotoxicity to cultivated plants and the herbicidal activity on weeds were evaluated as follows: the aereal parts of the test plants were cut off and weighed (fresh weight); the percentage of the fresh weight of the treated plant to that of the untreated plant was calculated with the latter fresh weight taken as 100; and the crop damage and the herbicidal activity were evaluated by the standard given in the table below. The rating values of phytotoxicity, 0 and 1, and those of herbicidal effect, 5 and 4, are generally regarded as satisfactory to protect cultivated plants and to control weeds, respectively. The rating values in the paddy rice test alone were calculated from the dry weight of the plant.

| Rating value | Fresh weight (percentage to untreated plot) | |
|---|---|---|
| | Cultivated plant | Weed |
| 5 | 0–39 | 0 |
| 4 | 40–59 | 1–10 |
| 3 | 60–79 | 11–20 |
| 2 | 80–89 | 21–40 |
| 1 | 90–99 | 41–60 |
| 0 | 100 | 61–100 |

The following control compounds were used in the Examples.

Control (a)

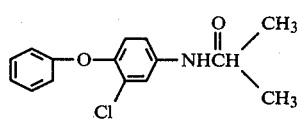

Control (b)

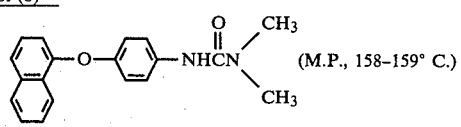

(M.P., 158–159° C.)

Control (c)

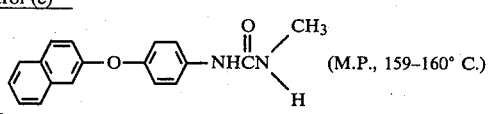

(M.P., 159–160° C.)

MCP

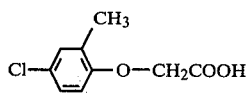

Barban

Bentazon

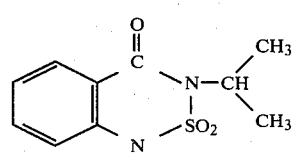

EXAMPLE A (Paddy rice test)

Wagner's pots (1/5000 are) were each filled with 1.5 kg of paddy field soil containing the seeds of weeds and kept under flooded conditions. The seedlings of rice plants at a 3-leaf stage were transplanted thereto, and after the seeds of barnyard grass were sowed therein, the seedlings were grown for 15 days in a green-house. Thereafter, the required amount of the wettable powder of each test compound was diluted with water and applied to the soil under flooded conditions. Twenty-five days after the application, the evaluation of herbicidal activity and phytotoxicity was made on the rice plants and barnyard grass as well as broadleaved weeds (e.g. pickerel weed (*Monochoria vagianalis*), false pimpernel (*Linderna pyxidaria*), toothcup (*Rotala indica* Koehne)) and nutsedge sp. (*Cyperus difformis*). The results are shown in Table 1.

TABLE 1

| Compound No. | Dosage (weight of active ingredient, g/are) | Evaluation of crop damage and herbicidal activity | | | |
|---|---|---|---|---|---|
| | | Rice plant | Barnyard grass | Broadleaved weed | Nutsedge sp. |
| 1 | 20 | 0 | 5 | 5 | 5 |
| | 10 | 0 | 4 | 5 | 5 |
| 2 | 20 | 0 | 4 | 5 | 5 |
| | 10 | 0 | 4 | 5 | 5 |
| 3 | 20 | 0 | 5 | 5 | 5 |
| | 10 | 0 | 4 | 5 | 5 |
| 4 | 20 | 0 | 4 | 5 | 5 |
| | 10 | 0 | 4 | 5 | 5 |
| 5 | 20 | 0 | 5 | 5 | 5 |
| | 10 | 0 | 4 | 5 | 5 |
| 6 | 20 | 0 | 4 | 5 | 5 |
| | 10 | 0 | 4 | 5 | 5 |
| 7 | 20 | 0 | 5 | 5 | 5 |
| | 10 | 0 | 4 | 5 | 5 |
| 8 | 20 | 0 | 4 | 5 | 5 |
| | 10 | 0 | 4 | 5 | 5 |
| Control (a) | 20 | 2 | 4 | 5 | 5 |
| | 10 | 1 | 3 | 5 | 4 |
| Control (b) | 40 | 0 | 0 | 4 | 2 |
| | 20 | 0 | 0 | 3 | 1 |
| Control (c) | 40 | 0 | 0 | 2 | 1 |
| | 20 | 0 | 0 | 0 | 0 |
| MCP | 20 | 3 | 3 | 5 | 5 |
| | 10 | 2 | 2 | 5 | 5 |

EXAMPLE B (Post-emergence application test (wheat))

Plastic trays (35 cm×25 cm×10 cm (high)) were filled with upland field soil, and the seeds of wheat, wild oat, water foxtail, large crabgrass, black nightshade, common lambsquarters, shepherd's-purse, catchweed bedstraw and chickweed were separately sowed in the trays and grown for 3 weeks in a green-house. The required amount of the test compound was sprayed to the foliage of the test plants over the top by means of a small hand sprayer. After the spraying, the test plants were grown for an additional 3 weeks in the greenhouse, and phytotoxicity and herbicidal activity were examined. The results are shown in Table 2. In the above foliar application, the test compounds were each formulated into an emulsifiable concentrate, and the required amount of the emulsifiable concentrate was dispersed in water for application at a spray volume of 5 liters per are and applied with the addition of a wetting agent. At the time of application, the wheat was in a 3-leaf stage and 12 cm in height. The weeds were in a 2- to 4-leaf stage and 2 to 12 cm in height although there was some difference depending upon the kind of weed.

EXAMPLE D (Pre-emergence application test)

TABLE 2

| Compound No. | Dosage (weight of active ingredient, g/are) | Phytotoxicity Wheat | Herbicidal activity | | | | | | |
|---|---|---|---|---|---|---|---|---|---|
| | | | Wild oat | Water foxtail | Large crabgrass | Black nightshade | Common lambsquarters | Shepherd's-purse | Catchweed bedstraw | Chickweed |
| 1 | 20 | 1 | 5 | 5 | 5 | 5 | 5 | 5 | 5 | 5 |
| | 10 | 0 | 5 | 5 | 5 | 5 | 5 | 5 | 5 | 5 |
| 2 | 20 | 0 | 5 | 5 | 5 | 5 | 5 | 5 | 5 | 5 |
| | 10 | 0 | 5 | 4 | 4 | 5 | 5 | 5 | 5 | 5 |
| 3 | 20 | 1 | 5 | 5 | 5 | 5 | 5 | 5 | 5 | 5 |
| | 10 | 0 | 5 | 5 | 4 | 5 | 5 | 5 | 5 | 5 |
| 4 | 20 | 0 | 5 | 5 | 5 | 5 | 5 | 5 | 5 | 5 |
| | 10 | 0 | 5 | 4 | 4 | 5 | 5 | 5 | 5 | 5 |
| 5 | 20 | 1 | 4 | 5 | 5 | 5 | 5 | 5 | 5 | 5 |
| | 10 | 0 | 4 | 5 | 5 | 5 | 5 | 5 | 5 | 5 |
| 6 | 20 | 0 | 4 | 5 | 5 | 5 | 5 | 5 | 5 | 5 |
| | 10 | 0 | 3 | 4 | 4 | 5 | 5 | 5 | 5 | 5 |
| Control (a) | 20 | 4 | 2 | 3 | 3 | 5 | 5 | 5 | 4 | 5 |
| | 10 | 3 | 1 | 2 | 2 | 5 | 5 | 5 | 4 | 5 |
| Control (b) | 40 | 1 | 0 | 0 | 0 | 4 | 3 | 3 | 2 | 3 |
| | 20 | 0 | 0 | 0 | 0 | 2 | 2 | 1 | 0 | 3 |
| Control (c) | 40 | 0 | 0 | 0 | 0 | 1 | 2 | 1 | 0 | 0 |
| | 20 | 0 | 0 | 0 | 0 | 0 | 1 | 0 | 0 | 0 |
| Barban | 20 | 1 | 5 | 2 | 2 | 0 | 1 | 2 | 1 | 2 |
| | 10 | 1 | 4 | 1 | 1 | 0 | 0 | 1 | 0 | 1 |

EXAMPLE C (Post-emergence application test (soybean))

According to the method of Example A, the phytotoxicity to soybean and the herbicidal activity against cocklebur, annual morningglory, jimsonweed, sunflower and redroot pigweed were examined. At the time of application, soybean was in a second trifoliate stage, and the weeds were in a 2- to 6-leaf stage and 3 to 20 cm in height although there was some difference depending upon the kind of weed. The results are shown in Table 3.

Plastic trays (35 cm × 25 cm × 10 cm (high)) were filled with upland field soil, and the seeds of rice, wheat, corn, soybean, peanut, cotton, sugar beet, water foxtail, large crabgrass, black nightshade, common lambsquarters, shepherd's-purse and redroot pigweed were sowed. The required amount of a wettable powder was dispersed in water and sprayed at a volume of 5 liters per are to the whole surface of the soil by means of a small hand sprayer. After the spraying, the trays were placed in a green-house for 20 days, and phytotoxicity and herbicidal activity were examined. The examination was carried out according to the same standard as above. The results are shown in Table 4.

TABLE 3

| Compound No. | Dosage (weight of active ingredient, g/are) | Phytotoxicity Soybean | Herbicidal activity | | | | |
|---|---|---|---|---|---|---|---|
| | | | Large crabgrass | Cocklebur | Annual morningglory | Jimsonweed | Sunflower | Redroot pigweed |
| 1 | 20 | 1 | 5 | 5 | 5 | 5 | 5 | 5 |
| | 10 | 0 | 5 | 5 | 5 | 5 | 5 | 5 |
| 2 | 20 | 0 | 5 | 5 | 5 | 5 | 5 | 5 |
| | 10 | 0 | 4 | 5 | 5 | 5 | 5 | 5 |
| 3 | 20 | 1 | 5 | 5 | 5 | 5 | 5 | 5 |
| | 10 | 0 | 4 | 5 | 5 | 5 | 5 | 5 |
| 4 | 20 | 1 | 5 | 5 | 5 | 5 | 5 | 5 |
| | 10 | 0 | 4 | 5 | 5 | 5 | 5 | 5 |
| 5 | 20 | 1 | 5 | 5 | 5 | 5 | 5 | 5 |
| | 10 | 0 | 4 | 5 | 5 | 5 | 5 | 5 |
| 6 | 40 | 0 | 4 | 5 | 5 | 5 | 5 | 5 |
| | 20 | 0 | 4 | 5 | 5 | 5 | 5 | 5 |
| Control (a) | 20 | 4 | 3 | 5 | 5 | 5 | 5 | 5 |
| | 10 | 4 | 2 | 4 | 4 | 5 | 5 | 5 |
| Control (b) | 40 | 0 | 1 | 3 | 3 | 4 | 0 | 4 |
| | 20 | 0 | 0 | 2 | 1 | 2 | 0 | 3 |
| Control (c) | 40 | 1 | 0 | 1 | 0 | 1 | 0 | 1 |
| | 20 | 0 | 0 | 0 | 0 | 0 | 0 | 1 |
| Bentazon | 20 | 1 | 0 | 5 | 4 | 5 | 5 | 1 |
| | 10 | 0 | 0 | 5 | 2 | 5 | 5 | 0 |

TABLE 4

| Compound No. | Dosage (weight of active ingredient, g/are) | Phytotoxicity | | | | | | | Herbicidal activity | | | | | |
|---|---|---|---|---|---|---|---|---|---|---|---|---|---|---|
| | | Rice | Wheat | Corn | Soybean | Peanut | Cotton | Sugar beet | Water foxtail | Large crabgrass | Black nightshade | Common lambsquarters | Shepherd's-purse | Redroot pigweed |
| 1 | 40 | 0 | 0 | 0 | 0 | 0 | 0 | 1 | 5 | 4 | 5 | 5 | 5 | 5 |
|   | 20 | 0 | 0 | 0 | 0 | 0 | 0 | 0 | 4 | 4 | 5 | 5 | 5 | 5 |
| 2 | 40 | 0 | 0 | 0 | 0 | 0 | 0 | 0 | 4 | 4 | 5 | 5 | 5 | 5 |
|   | 20 | 0 | 0 | 0 | 0 | 0 | 0 | 0 | 4 | 3 | 5 | 5 | 5 | 5 |
| 3 | 40 | 0 | 0 | 0 | 0 | 0 | 1 | 1 | 5 | 4 | 5 | 5 | 5 | 5 |
|   | 20 | 0 | 0 | 0 | 0 | 0 | 0 | 0 | 4 | 4 | 5 | 5 | 5 | 5 |
| 4 | 40 | 0 | 0 | 0 | 0 | 0 | 0 | 0 | 4 | 4 | 5 | 5 | 5 | 5 |
|   | 20 | 0 | 0 | 0 | 0 | 0 | 0 | 0 | 4 | 4 | 5 | 5 | 5 | 5 |
| 5 | 40 | 0 | 0 | 0 | 0 | 0 | 0 | 1 | 5 | 4 | 5 | 5 | 5 | 5 |
|   | 20 | 0 | 0 | 0 | 0 | 0 | 0 | 0 | 4 | 4 | 5 | 5 | 5 | 5 |
| 6 | 40 | 0 | 0 | 0 | 0 | 0 | 0 | 0 | 4 | 4 | 5 | 5 | 5 | 5 |
|   | 20 | 0 | 0 | 0 | 0 | 0 | 0 | 0 | 3 | 3 | 5 | 5 | 5 | 5 |
| Control (a) | 40 | 0 | 0 | 0 | 1 | 1 | 2 | 3 | 3 | 2 | 5 | 5 | 5 | 5 |
|   | 20 | 0 | 0 | 0 | 0 | 0 | 1 | 2 | 1 | 1 | 4 | 4 | 5 | 5 |
| Control (b) | 40 | 0 | 0 | 0 | 0 | 0 | 1 | 0 | 2 | 1 | 4 | 4 | 3 | 4 |
|   | 20 | 0 | 0 | 0 | 0 | 0 | 0 | 0 | 1 | 0 | 3 | 2 | 3 | 2 |
| Control (c) | 40 | 0 | 0 | 0 | 0 | 0 | 0 | 0 | 0 | 0 | 1 | 2 | 1 | 2 |
|   | 20 | 0 | 0 | 0 | 0 | 0 | 0 | 0 | 0 | 0 | 0 | 0 | 0 | 1 |

The application of the compounds (I) as fungicides will be illustrated in the following Example wherein a commercially available fungicide known under the generic name "triforine" and having the following formula was used for comparison:

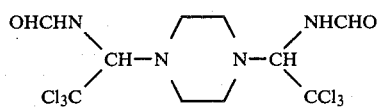

EXAMPLE E (Protective effect on leaf rust of wheat)

Wheat (var.: Nohrin No. 61) was grown up to the one-leaf stage in a flower pot of 9 cm in diameter, inoculated with *Puccinia recondita* and placed in a humid chamber for 18 hours. Then, each of the emulsifiable concentrates containing the test compounds was diluted with water and sprayed on the test plants at a rate of 15 ml/pot. The test plants were placed in a chamber kept at 20° C. and grown under a fluorescent lamp for an additional 10 days. The infection state was observed, and the disease severity was calculated on the basis of the following standard:

| Disease index | Infection state |
|---|---|
| 0 | No infectious spot on the examined leaf |
| 1 | Less than 10 infectious spots on the examined leaf |
| 2 | 11–20 infectious spots on the examined leaf |
| 4 | 21–50 infectious spots on the examined leaf |
| 8 | More than 51 infectious spots on the examined leaf |

$$\text{Disease severity (\%)} = \frac{\Sigma(\text{Disease index}) \times (\text{Number of leaves})}{8 \times (\text{Total number of leaves examined})} \times 100$$

The results are shown in Table 5.

TABLE 5

| Compound No. | Concentration of active ingredient (ppm) | Disease severity (%) |
|---|---|---|
| 5 | 500 | 5.2 |
| 6 | 500 | 4.8 |
| Triforine | 500 | 7.0 |
| Untreated | — | 100.0 |

What is claimed is:

1. A herbicidal composition which comprises as an active ingredient a herbicidally effective amount of a compound of the formula:

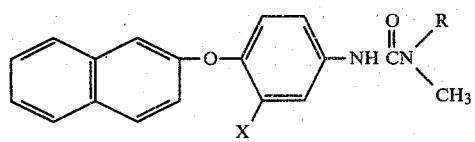

wherein X is a hydrogen atom, a halogen atom or a trifluoromethyl group and R is a methyl group or a methoxy group, and an inert carrier.

2. The composition according to claim 1, wherein X is a hydrogen atom, a chlorine atom, a bromine atom, a fluorine atom or a trifluoromethyl group.

3. The composition according to claim 1, wherein X is a hydrogen atom and R is a methoxy group.

4. A method for controlling weeds which comprises contacting the weeds with a compound of the formula:

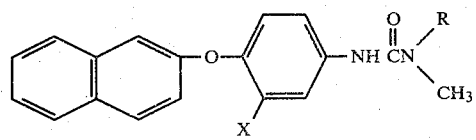

wherein X is a hydrogen atom, a halogen atom or a trifluoromethyl group and R is a methyl group or a methoxy group.

5. The method of claim 4, wherein X is a hydrogen atom, a chlorine atom, a bromine atom, a fluorine atom or a trifluoromethyl group.

6. The method of claim 4, wherein X is a hydrogen atom and R is a methoxy group.

7. A method for selectively combating weeds in the cultivation of soybean and/or gramineous crops, which comprises applying to the area wherein said crops are cultivated a herbicidally effective amount of a compound of the formula:

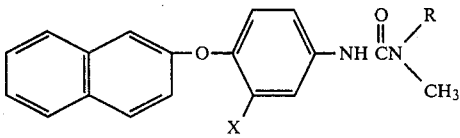

wherein X is a hydrogen atom, a halogen atom or a trifluoromethyl group and R is a methyl group or a methoxy group.

8. The method of claim 7, wherein X is a hydrogen atom, a chlorine atom, a bromine atom, a fluorine atom or a trifluoromethyl group.

9. The method of claim 7, wherein X is a hydrogen atom and R is a methoxy group.

* * * * *

UNITED STATES PATENT AND TRADEMARK OFFICE
CERTIFICATE OF CORRECTION

PATENT NO. : 4,280,835
DATED : July 28, 1981
INVENTOR(S) : Takemoto et al.

It is certified that error appears in the above—identified patent and that said Letters Patent is hereby corrected as shown below:

In the category entitled "[75] Inventors", line 1 thereof, change "Takemoto Ichiki" to --Ichiki Takemoto-- and line 3 thereof, change "Kamoshita Katsuzo" to --Katsuzo Kamoshita--.

Signed and Sealed this

*Twentieth* Day of *October 1981*

[SEAL]

Attest:

GERALD J. MOSSINGHOFF

*Attesting Officer*  *Commissioner of Patents and Trademarks*